United States Patent [19]
Eseifan et al.

[11] Patent Number: 4,589,417
[45] Date of Patent: May 20, 1986

[54] APPARATUS FOR SELECTIVE MEASURING AND TREATING DISORDERED TISSUES

[76] Inventors: Ali H. Eseifan, 90 Randolph Ave., South San Francisco, Calif. 94080; Laurence E. Badgley, 370 San Bruno Ave. West, San Bruno, Calif. 94066

[21] Appl. No.: 648,818

[22] Filed: Sep. 10, 1984

[51] Int. Cl.⁴ .............................................. A61N 1/32
[52] U.S. Cl. ..................................... 128/422; 128/741
[58] Field of Search ..................... 128/1.5, 419 R, 421, 128/422, 423, 804, 732, 741, 687

[56] References Cited

U.S. PATENT DOCUMENTS

| | | | |
|---|---|---|---|
| 2,658,505 | 11/1953 | Sheer | 128/687 |
| 4,056,097 | 11/1977 | Maass | 128/419 C |
| 4,166,454 | 9/1979 | Meijer | 128/689 |
| 4,399,821 | 8/1983 | Bowers | 128/421 |

FOREIGN PATENT DOCUMENTS 2092004  8/1982  United Kingdom ............... 128/421

Primary Examiner—William E. Kamm
Attorney, Agent, or Firm—T. R. Zegree

[57] ABSTRACT

A portable medical apparatus for use in diagnosing, testing and/or treating simultaneously various types of body disorders, including neurological or muscular abnormalities, by non-invasive and painless procedure comprising essentially an amplifier interconnected with a sensor, a meter, a threshold control, an electronic driver, a transducer and a power supply in the form of a low-voltage battery, stimulates living tissue by electromagnetic energy produced thereby for transmission thereof to the afflicted portion of patient's body.

14 Claims, 4 Drawing Figures

APPARATUS FOR SELECTIVE MEASURING AND TREATING DISORDERED TISSUES

BACKGROUND OF THE INVENTION

The present invention relates to an apparatus for use in measuring and/or treating selectively disordered tissues in human or animal body. More particularly, the invention relates to a medical apparatus for testing and/or treating afflicted area of human body by inducing electrical, electromagnetic or other forms of stimulation of the area to be tested or treated.

As is well known, various parts of the human body, such as muscles, nerves, organs and other soft or hard tissues can be electrically stimulated by different electronic devices designed to measure electrical potentials thereof. For instance, medical devices known as electromyographs have been used in research and for teaching purposes on muscular activity. Other devices, known as bio-feedback systems, are adapted to measure physiological activity of a person and to perform physical therapy based on monitored electric signals. These and other related devices have been described, for example in U.S. Pat. Nos. 2,712,975 to Golseth et al.; 3,641,993 to Gaarder; 3,817,254 to Maurer; 3,916,876 to Freeman; 4,170,225 to Criglar et al.; 4,177,819 to Kofsky et al.; 4,249,537 to Lee et al.; 4,340,063 to Maurer; and 4,434,798 to Trnkoczy et al. Moreover, three related to each other U.S. Pat. Nos. 4,105,017, 4,266,532 and 4,266,533 to Ryaby et al. disclose devices for altering the growth, repair and maintenance behavior of living tissues and/or cells, particularly bones, by subjecting the desired area of the body to a specifically encoded voltage and concomitant current.

While the above-mentioned prior art patents describe various forms of devices generating pulses for stimulation and control of contraction of muscles and other living tissues, we have developed a new device which encompasses a distinct approach in the diagnosis and treatment of muscular and other tissue disorders not heretofore known in the art.

OBJECTS OF THE INVENTION

Accordingly, it is the primary object of the invention to provide an apparatus adapted for use in selective measurement and treatment of human or animal body oscillation by accurate stimulation thereof and in the simultaneous treatment of the afflicted portion of the body.

Another object of the invention is to provide a portable, compact device capable of changing electric to electromagnetic energy or another type of energy in monitoring and treating a disordered area of patient's body after a diagnosis based on the read-out of the device has been made.

A further object of the invention is the provision of a self-powered medical apparatus which is versatile in performing various functions, i.e. treatments or measurements alone or simultaneous measurements and treatments of individual points or areas of the body.

A still further object of the invention is to provide an easy to operate apparatus which functions as a non-invasive precision stimulator in testing and treating various types of pain in the body by application of natural electromagnetic field.

These and other objects of the invention will become more fully apparent from the following description taken in connection with the accompanying drawing.

BRIEF SUMMARY OF THE INVENTION

In accordance with the invention there is provided an apparatus adapted for measuring an afflicted area of a body and for simultaneous treatment of said area comprising, in combination:
 (a) amplifier means;
 (b) sensor means electrically connected to said amplifier means and releasably attachable to said area of the body to be tested;
 (c) meter means electrically connected to said amplifier means;
 (d) threshold control means electrically connected to said amplifier means;
 (e) electronic driver means electrically connected to said amplifier means;
 (f) transducer means electrically connected to said driver means for conversion of electrical energy to another type of energy, said transducer means being releasably attachable to said afflicted area; and
 (g) a power supply electrically connected to said apparatus for providing energy to said body.

The apparatus may additionally include a switch means connecting electrically said amplifier means and said driver means; and
 (h) shape and frequency control means;
 (i) oscillator means electrically connected to said shape and frequency control means and to said switch means; and
 (j) frequency counter means electrically connected to said oscillator means.

BRIEF DESCRIPTION OF THE DRAWINGS

The invention will now be more fully described with reference to the accompanying drawings, wherein.

DETAILED DESCRIPTION

Figure 1:
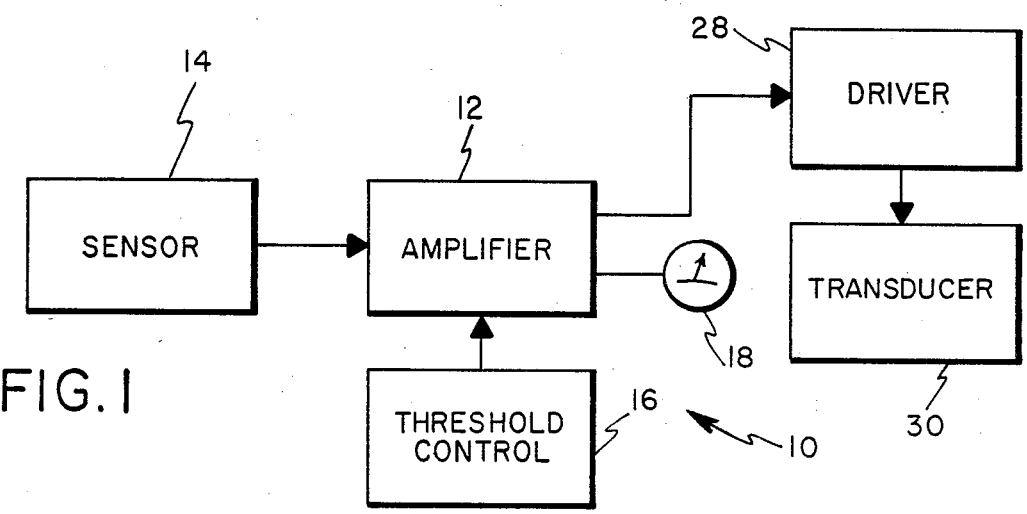
FIG. 1 illustrates the electrical circuitry according to one embodiment of the invention in the form of a functional block diagram.

Referring now to the drawings, FIG. 1 illustrates the essential elements of the circuitry 10 which comprise an amplifier 12 for increase of the strength of electrical signals, a sensor 14 connected to the input thereof, a threshold control 16, likewise connected to amplifier 12, for control of sensitivity of signals transmitted to the input of amplifier 12 to a desired level and for selection of a portion of a signal to be amplified. Threshold control 16 is in the form of a variable resistor of from 0 to about 10,000 ohms value or higher, if desired. A meter 18, connected to amplifier 12, is a milliammeter of from 0 to 1 milliamps used for measurement of the strength of electric current. Amplifier 12 is adapted to receive the magnitude, shape and frequency of pulses sensed by sensor 14. It is also connected to driver 28 directly by interfacing the input of driver 28 with the output of amplifier 12. The circuitry is completed by transducer 30 which is linked with electronic driver 28 and provided with a suitable device (not shown) for detachably securing it to the surface of the body of a patient to be treated, such as a small disc adhesively coated on both faces thereof. Although one driver is adequate for some applications, a plurality of drivers linked in parallel, i.e. as many as thirty or even more, can be employed, if desired or required for other applications. Transducer 30 is specifically adapted to convert electrical energy to another type of energy, such as electromagnetic, mechanical, sound/ultrasonic, chemical, pressure, infrared ultraviolet and others. Driver 28 is used in the circuitry for interfacing between the components of the system so that they are adapted to each other. Moreover, driver 28 is capable of increasing the voltage and the current from the output of oscillator 22 (which will be referred to hereinafter) to the input of transducer 30. Power supply (not shown) for the apparatus is in the form of a rechargeable battery having a voltage of from 4 to 24 volts or higher, if desired. However, a 6-volt battery is usually satisfactory.

It is to be noted that the apparatus of the invention is operated on a battery exclusively to prevent possible transmission of an electric shock to the patient if power were supplied directly from a 110 or 220 volt electrical outlet.

The apparatus described hereinabove, designated hereinafter as System A, represents a high resolution instrument useful in monitoring and treating simultaneously a disordered area of patient's body. It is particularly adapted to measure smooth muscle tension of arterial tissues. Moreover, it is capable of picking up faint signals from the pulse in a suitable location, such as the radial artery, by attaching sensor 14 which may be in the form of a capacitor microphone or the like on the wrist in the vicinity thereof. The magnitude, shape and frequency of the pulse are transmitted to amplifier 12 and read on meter 18. Transducer 30 is likewise adhesively attached to the surface of patient's body adjacent the pain point. The System A, designed for use in V. A. S. (Vascular Autonomic Signal) mode is advantageous as it receives natural body rythms directly in actual time period.

Figure 2:
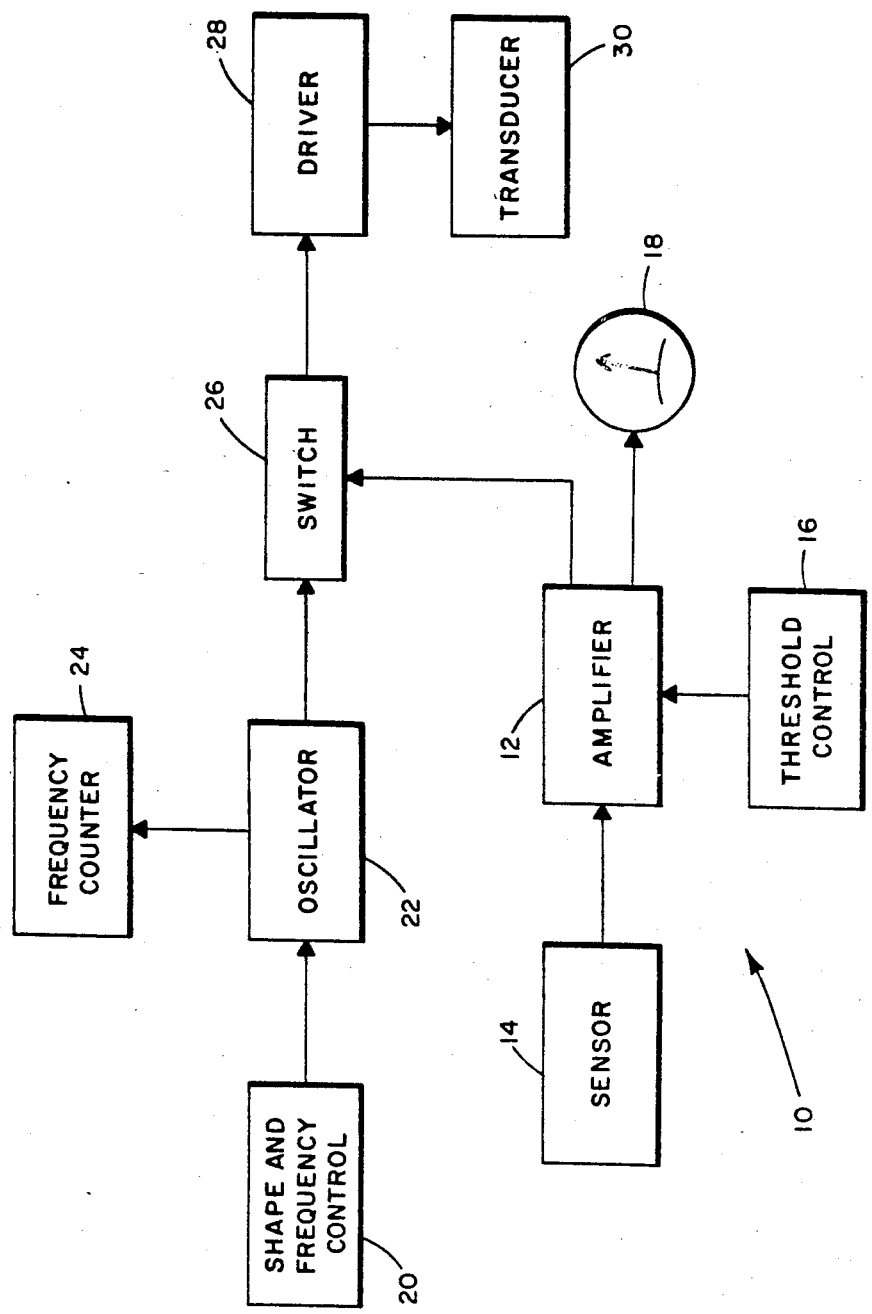

In another embodiment of the invention, illustrated in FIG. 2 and designated as System B, the circuitry of System A is linked with three additional elements, i.e. a shape and frequency control 20 which is operable to regulate the shape of frequency and the frequency of pulse generated by oscillator 22 connected thereto and a frequency counter 24 or digital read-out connected to oscillator 22 which is connected through a manually operable switch 26 to driver 28. Amplifier 12 is likewise connected to driver 28 through the same switch 26. Frequency counter 24 is adapted to display frequency generated by the apparatus to the nearest 0.1 hertz. The apparatus of System B is equally highly effective in both measuring and treating afflicted portions of the body. It is capable of producing its own dialed frequency or patient's radial artery pulses on five power outputs which can be obtained through a 3.5 mm. phone plug. The five outputs provided in System B enable a simultaneous treatment of five different locations in the patient's body. Oscillator 22, the frequency of which spans from 0 to 500 hertz or more in increments of 0.1 hertz is employed to feed the electromagnetic heads applied to pain area of the patient's body so that custom-made treatments of the selected area can be achieved. The System B is designated as the oscillator mode.

Figure 3:
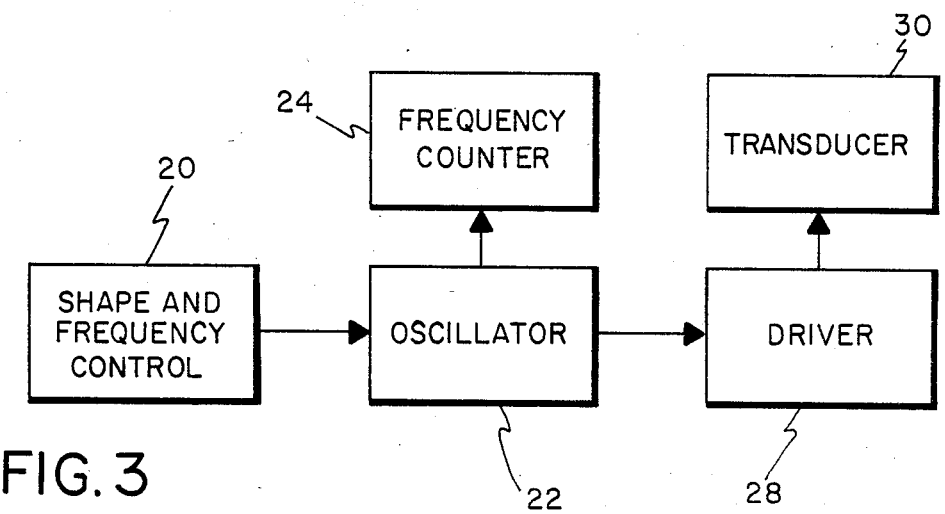
FIGS. 2, 3 and 4 illustrate circuitries of three other embodiments of the invention likewise in functional block diagram.

Besides the Systems A and B described hereinabove, a part of the circuitry 10, shown in FIG. 3 and referred to as System C, may be used for treatment alone of an afflicted area of the body. Thus System C comprises shape and frequency control 20 responsive to linear oscillator 22 connected thereto, frequency counter 24 connected to oscillator 22, electronic driver 28 which may be connected directly to oscillator 22 or through switch 26, as shown in FIG. 3, and transducer 30 connected to driver 28 and being provided with a small disc adhesively coated on both faces thereof for releasable attachment of transducer 30 to the afflicted area of the body to be treated. Accordingly, the System C is useful for treating disorders in cases where a diagnosis has been made and measurements are not required.

Figure 4:
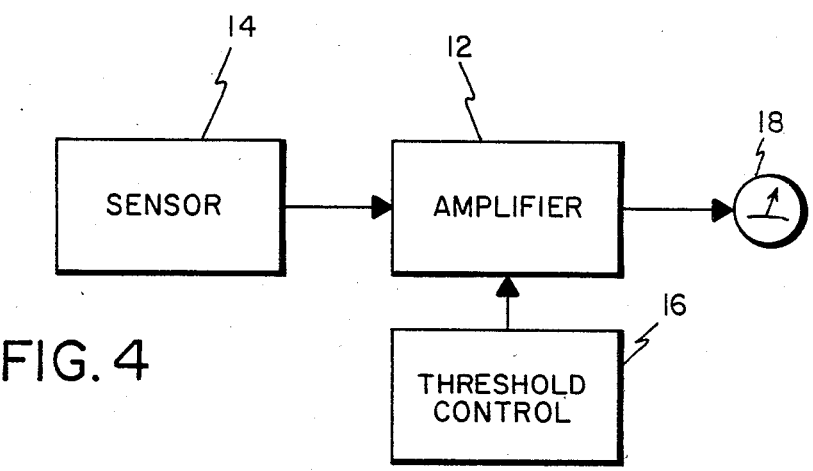

In another embodiment, the apparatus of this invention illustrated in FIG. 4 can also function for testing alone of an area of patient's body. Such embodiment, encompassing also a part of the overall circuitry 10 and defined as System D comprises amplifier 12, sensor 14 connected thereto and provided with an adhesively coated disc for its attachment to the location to be tested, meter 18 connected to amplifier 12 and threshold control 16 connected to amplifier 12, the specifics of all the individual elements of the System D having been explained hereinabove. The advantage of the System D unit is that measurements of an afflicted area of the body can be effected for diagnostic purposes only in cases where immediate treatment may not be required.

It will be noted that each of the four Systems described herein is provided with its power supply in the form of a low-voltage battery.

The apparatus of the invention may be mounted in a single housing provided with clearly indicated panel markings of the components, manually operable switch levers on the outside and the entire electronic circuitry mounted in the interior of the housing. In the altenative, the circuitry may be mounted in two separate housings, one containing electronic components of System C and the other containing the components of System D, such housings being either connected electrically thus forming System B or independent from each other. The frequency counter 24 or digital frequency display may likewise be mounted in a third housing interconnected with the housing containing the oscillator.

The entire unit is portable, relatively light as it weighs less than 5 kilograms, easy and safe to operate. The housings are fabricated from a durable, rigid plastic material with metallic front panels having all the outlets marked for easy identification by the operator.

It is to be understood that the circuitry described hereinabove includes several conventional and readily available essential elements which are connected by flexible conductors in the usual manner known to persons skilled in the art. Therefore, a more detailed description of such elements and other standard electronic components is deemed unnecessary. Likewise, the mode of operation of the apparatus is very simple and readily understood by those skilled in the art.

It should also be noted that various wave forms can be produced by the circuitry according to the invention. Such forms include square wave or pulse and their inversion, ramp and ramp types and their inversions and sine wave. The apparatus is adapted to use all alternating wave forms which can be transformed by induction or passed through a capacitor.

Various types of afflictions or ailments may be treated with the apparatus of the invention, including headache, migraine, facial palsy, sciatica, gastro-intestinal disorders, dysfunctions of body organs and many other neurological or muscular abnormalities. Repeated treatments for a short period of time result in reducing the affliction, relief of pain and in accelerating regeneration and healing of soft and hard tissues.

It will be apparent from the foregoing description that we have devised a novel, portable medical apparatus specifically adapted for testing, monitoring and treating simultaneously various parts of human or animal body, particularly soft tissues. Such functions can be performed with our apparatus which converts electrical energy to another type of energy, particularly to electromagnetic energy which, in turn, causes stimulation of a portion of patient's body for a predetermined period of time by a non-invasive, safe and painless procedure. The apparatus is characterized by a new combination of electronic elements which is highly advantageous in achieving its basic functions as described hereinabove and by versatility which permits the use of the apparatus in its entirety or certain selected portions thereof depending on whether testing and/or treating is contemplated.

It will be understood that various modifications in the form or in the structural details of our invention as herein described may be made without departing from the spirit thereof or the scope of the claims which follow.

We claim:

1. Apparatus adapted for measuring an afflicted area of a body and for simultaneous treatment of said area comprising, in combination:
   (a) amplifier means;
   (b) sensor means electrically connected to input of said amplifier means and means for releasably attaching said sensor means to said area of the body to be tested;
   (c) meter means electrically connected to output of said amplifier means;
   (d) threshold control means electrically connected to input of said amplifier means;
   (e) electronic driver means electrically connected to output of said amplifier means; and
   (f) transducer means electrically connected to output of said driver means for conversion of electrical energy to another type of energy, said transducer means being releasably attachable to said afflicted area.

2. The apparatus of claim 1 wherein said amplifier means is adapted to receive the magnitude, shape and frequency of pulses sensed by said sensor means.

3. The apparatus of claim 1 wherein said sensor means comprises a capacitor microphone.

4. The apparatus of claim 1 wherein said sensor means is attachable to the body of a patient by an adhesively coated disc disposed on both faces thereof.

5. The apparatus of claim 1 wherein said threshold control means is in the form of a variable resistor of from 0 to about 10,000 ohms.

6. The apparatus of claim 1 wherein said meter means comprises a milliammeter of from 0 to about 1 milliamp.

7. The apparatus of claim 1 wherein said electronic driver means is connected to said amplifier means by interfacing by means of a switch the input of said driver means with the output of said amplifier means.

8. The apparatus of claim 1 wherein said transducer means converts electrical energy to electromagnetic energy.

9. Apparatus of claim 1 wherein said electronic driver means includes a plurality of drivers linked in parallel.

10. Apparatus of claim 1 including a switch means connecting electrically said amplifier means and said driver means.

11. Apparatus of claim 10 including:
    (h) shape and frequency control means;
    (i) oscillator means electrically connected to said shape and frequency control means and to said switch means; and
    (j) frequency counter means electrically connected to said oscillator means, wherein said shape and frequency control means regulates the shape and frequency and the frequency of pulse generated by said oscillator means.

12. The apparatus of claim 1 wherein power supply therefor is in the form of a low-voltage battery.

13. Apparatus for treatment of afflicted area of a body comprising, in combination:
    shape and frequency control means;
    oscillator means electrically connected to said shape and frequency control means;
    frequency counter means electrically connected to said oscillator means; and transducer means electrically connected to electronic driver means and provided with means for releasably attaching to said afflicted area.

14. Apparatus for testing an area of a body for diagnostic purposes comprising, in combination:
    amplifier means;
    sensor means electrically connected to said amplifier means and releasably attachable to said area to be tested;
    meter means electrically connected to said amplifier means; and threshold control means electrically connected to said amplifier means.

* * * * *